United States Patent [19]
Garnier

[11] 4,217,098
[45] Aug. 12, 1980

[54] DEVICE FOR LIMITING THE PENETRATION OF DENTAL ROOT CANAL INSTRUMENTS

[75] Inventor: Marcel Garnier, Besancon, France

[73] Assignee: Micro-Mega S.A., Besancon, France

[21] Appl. No.: 784,447

[22] Filed: Apr. 4, 1977

Related U.S. Application Data

[63] Continuation of Ser. No. 588,717, Jun. 20, 1975, abandoned.

[30] Foreign Application Priority Data

Jul. 30, 1974 [FR] France .................... 74 26455

[51] Int. Cl.² ............................................. A61C 3/00
[52] U.S. Cl. ................................ 433/147; 433/102
[58] Field of Search ......................... 408/241 S, 211;
32/40 R, 57, 69, 23, 48, 49, 29

[56] References Cited

U.S. PATENT DOCUMENTS

| 2,210,128 | 8/1940 | Rohr | 408/112 |
| 3,838,517 | 10/1974 | Michnick | 32/27 |

FOREIGN PATENT DOCUMENTS 2228463  12/1974  France ............................. 32/29

*Primary Examiner*—Robert Peshock
*Attorney, Agent, or Firm*—Robert E. Burns; Emmanuel J. Lobato; Bruce L. Adams

[57] ABSTRACT

A centrally-bored cylindrical abutment member is fitted over the shank of a root canal instrument and held against the instrument handle or head by elastic clipping means acting on the instrument handle, or on a handpiece carrying the instrument. The thickness of the abutment member may be adjustable, e.g. by screwing, or several interchangeable devices with abutment members of different thicknesses can be provided to accurately set the effective penetrable length of the instrument.

6 Claims, 8 Drawing Figures

DEVICE FOR LIMITING THE PENETRATION OF DENTAL ROOT CANAL INSTRUMENTS

This is a continuation of application Ser. No. 588,717, filed June 20, 1975 and now abandoned.

The invention relates to devices for limiting the penetration of endodontic instruments during the treatment of root or pulp canals.

Dental surgeons sometimes have to excavate pulp cavities, and replace the pulp by an antiseptic insulating material. The placing of this material involves enlargement of the root canal by boring or reaming.

To carry out this boring for extraction of the pulp, dental surgeons use root canal instruments such as nerve broaches, smooth or square broaches, so called Kerr files and reamers, Haedstrom files, and so on.

Boring is carried out by reaming the root canal walls, the cutting parts of the instrument scraping pieces of dentine from the tooth wall, by either manually or mechanically rotating the instrument and simultaneously moving it longitudinally towards the apex.

When operating without an anesthaesic, as soon as the instrument arrives at the apex, the patient's reaction to pain warns the practician. However, when operating under an anasthaesic, the patient does not react and the instrument may pass the apex and damage the bottom of the cavity, and create a risk of infection.

For this purpose, an abutment is placed on the instrument to limit penetration and prevent the point arriving at the apex. The depth of the canal can be determined by radiography, and an ideal precision of the order of several tenths of a millimeter can be achieved.

Various devices have already been used for this purpose. A simple, early expedient was to place one or several rubber rings or washers on the instrument shank, to serve as a reference. However, the manual placing of such washers is delicate and various devices have been employed to ease this fitting. Nevertheless, these washers do not always satisfactorily stay in place, and are thus liable to be moved during operation.

A second known device involves adjustably fitting the instrument shank in a handle with, for example, a gripping nut arranged to fix the shank in place. To enable a useful range of adjustment of the length, the handle must be relatively long which makes it clumsy, especially for operations on the rearmost molars where operating space is limited. Also, these known arrangements are somewhat complex.

Another proposal (U.S. Pat. No. 3,562,913) has been to fit spring clips in calibrated ribs on the instrument shank, or to provide a nut screwed on a threaded part of the shank. These devices, however, considerably complicate manufacture of the root-canal instrument, and the ribs or thread on the shank may unwantedly act against the tooth being treated.

Yet another proposal has been to provide metal sleeves of various lengths having an internal rubber washer by which they can grip on an instrument shank. However, the grip is liable to deteriorate, especially when a sleeve has been fitted on a thick shank so that when later fitted on a slender shank it is liable to slip.

An object of the invention is therefore to provide a device for attachment to a dental root canal instrument of the type having an enlarged head and a narrow elongated shank protruding from said head to an operative end, to limit its effective length of penetration, and which avoids the stated disadvantages and inconveniences.

A device according to the invention comprises an abutment member having opposite first and second faces and means defining a bore passing through said first and second faces for passage of said shank through said abutment member, and means for elastically clipping said member at least indirectly to said instrument at a location remote from said shank to hold said first surface against said enlarged head and said second surface at a given distance from said head thereby limiting the effective penetrable length of the shank from said operative end to said second surface.

The abutment member may have an adjustable thickness; alternatively several devices with abutment members of different thicknesses can be provided.

The device may be fitted either to a hand-held root canal instrument such as a nerve broach, or to a handpiece of the "contraangle" type carrying the instrument. Mounting of the device on the instrument or on the head of a handpiece, and removal, can be carried out very easily and quickly (in about two to five seconds), which is important for the practitioner who must have rational tools with which no time is needlessly lost.

Several embodiments of the invention are shown, by way of example, in the accompanying drawings, in which.

Figure 1:
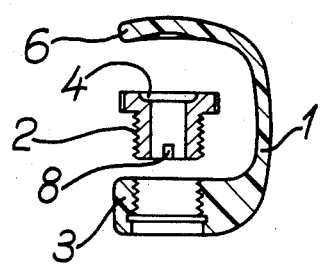
FIG. 1 is an exploded cross-sectional view of a first embodiment.
Figure 2:
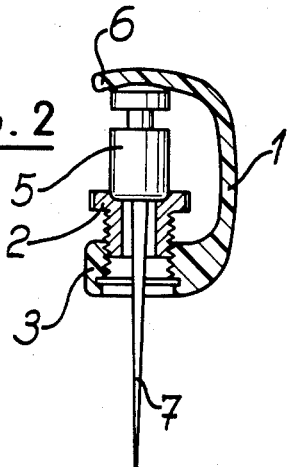
FIG. 2 shows the device of FIG. 1 fitted on a root canal instrument.

The embodiment of FIGS. 1 and 2 comprises a yoke-like body 1 having a thickened end 3 with a tapped bore forming a nut, and a thin flexible dished end 6 facing end 3. An externally screw threaded sleeve 2 having an enlarged head or flange is screwed in the end of the bore facing end 6. The cooperating threads are arranged to provide a tight fit. Sleeve 2 has an enlarged head or flange with a recessed upper face 4, and a slot 8 in its other end screwed in nut 3.

The device can be rapidly clipped on a hand-held root canal instrument such as a nerve broach comprising a handle 5 and a shank 7, as shown in FIG. 2, with the shank 7 passing through the bores of sleeve 2 and nut 3. The forward end of handle 5 fits in recessed face 4, which centres the shank 7 in the bore of sleeve 2, and the rear end of handle 5 fits against dished end 6 of body 1 which, by elastic deformation, firmly holds the instrument, the end 6 being elastically urged towards end 3. The effective penetrable length of shank 7 is limited by the outer abutment-forming face of nut 3, and can be adjusted by turning sleeve 2 by means of an appropriate tool engaging in slot 8. In use, the handle 5 is held between the surgeons thumb and index finger and can be turned without obstruction by the body 1 or sleeve 2.

The effective length of shank 7 is adjustable over a given range limited by fully screwing sleeve 2 in nut 3 and by unscrewing sleeve 2 to a position in which it still firmly engages in the nut. In a preferred form, the threaded part of nut 3 extends over from 5 to 6 mm, and the flange of sleeve 2 has a thickness of about 1 mm. It is thus possible to adjust the effective length of shank 7 over a range of about 4 mm, since about 2 mm of the screw and nut must remain in engagement to provide a firm hold.

As root canal instruments are generally manufactured with shank lengths of 21, 25 and 29 mm, it is possible to obtain operative shank lengths of from about 11 to 15 mm for a 21 mm instrument, from about 15 to 19 mm for a 25 mm instrument, and from about 19 to 23 mm for a 29 mm instrument.

Figure 3:
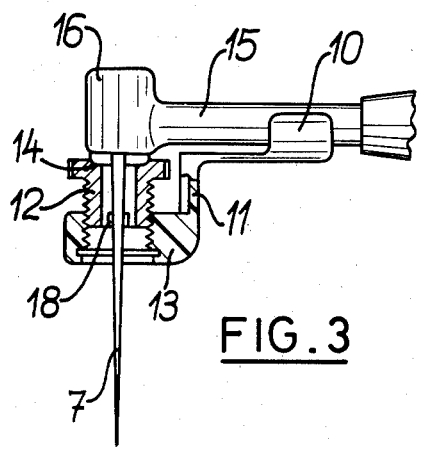
FIG. 3 is a cross-sectional and side-elevational view of a second embodiment fitted on a handpiece.

Such a device may also be fitted on a handpiece (such as 15, FIG. 3), in which case dished end 6 applies against the upper part of the handpiece head (as 16, FIG. 3). A varied form of device, for attachment to a handpiece 15 is shown in FIG. 3. In this case a resilient body 11 includes a stem transverse to the bores of nut 13 and sleeve 12, this stem carrying elastic tabs 10 in the form of a split ring which clips about the handpiece 15.

Sleeve 12 has an upper flange with a recessed face 14 which bears against the lower face of the handpiece head.

Figure 4:
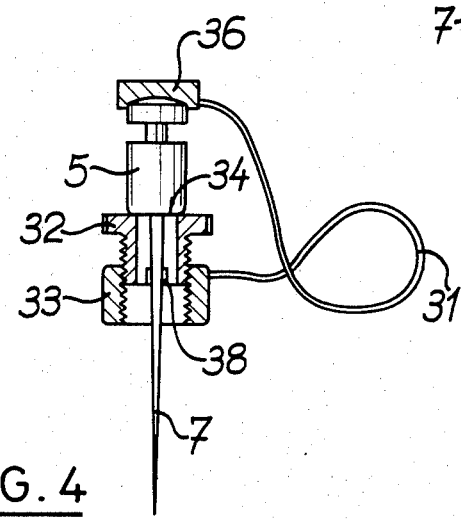
FIG. 4 is a cross-sectional and side-elevational view of a third embodiment fitted on a root-canal instrument.

FIG. 4 shows another embodiment comprising a recurvate spring clip 31 formed as loop and carrying at one end a nut 33 and at its other end a dished clipping member 36 facing nut 33. A flanged externally threaded sleeve 32 with a slot 38 is screwed by its slotted end in nut 33. This spring loop provides a greater elastic force to fit the device on an instrument, and is easier to manipulate.

Figure 5:
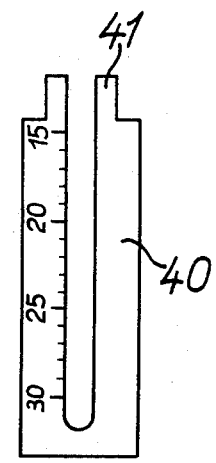
FIG. 5 is an elevational view of a tool for setting the first three embodiments.

Adjustment of the position of sleeves 2, 12 and 32 of the described embodiments is advantageously carried out by means of the tool 40 shown in FIG. 5. Tool 40 has a narrow end 41, forming a screw driver for engagement with slots 8, 18, 38, and a central opening which fits about shank 7. The tool is graduated so that, by engaging it against nut 3, 13 or 33, the distance from the end of the shank to the abutment face of the nut can be easily measured when adjusting the position of the nut.

Figure 6:
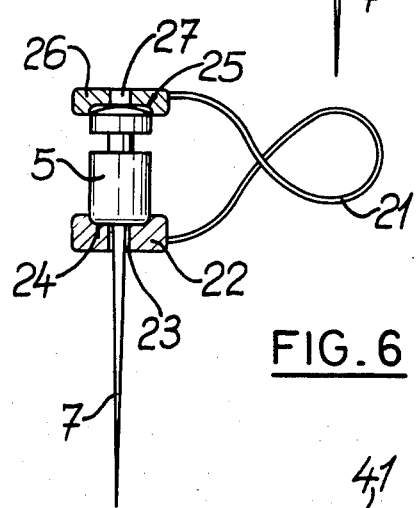
FIGS. 6 and 7 are cross-sectional and side-elevational views of fourth and fifth embodiments fitted on a root-canal instrument.

FIG. 6 shows a fourth embodiment comprising a looped spring clip 21 carrying abutment members 22, 26 at its two ends, these members respectively having central bores 23, 27 for passage of shank 7 and a dished surface 24, 25 for centring the respective end of handle 5. The ends of handle 5 are thus clipped between members 22, 26, the shank passing through bore 23, as shown, or bore 27. Each member 22, 26 has a given thickness, different to one another, to provide two settings of the penetrable length of shank 7 by turning the device around on the instrument handle 5.

Hence with four devices respectively having the following thicknesses of the abutment members: 1.5 and 2 mm; 2.5 and 3 mm; 3.5 and 4 mm; and 4.5 and 5 mm, and standard root canal instruments with shank lengths of 21, 25 and 29 mm, it is possible to obtain all operative shank lengths between 16 and 27.5 mm in steps of 0.5 mm.

To facilitate identification, clips with respectively one, two, three and four loops can be provided for the four devices.

Figure 7:
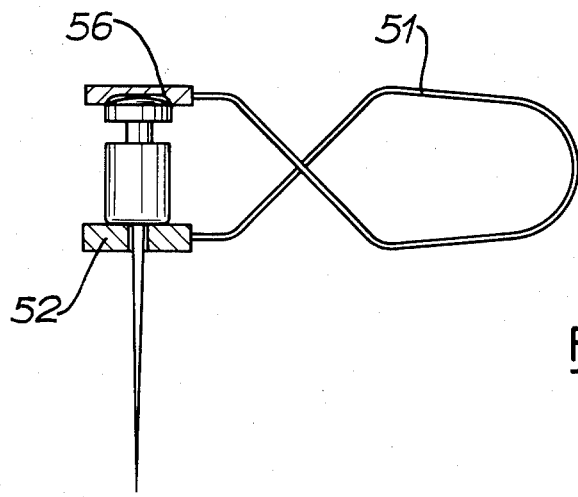

FIG. 7 shows a variation of the embodiment of FIG. 6, comprising a looped spring clip 51 carrying a centrally bored abutment member 52 of given thickness at one end and a dished clipping or bearing member 56 at its other end. In use, the ends of the instrument handle are clipped between members 56 and 52, with the shank passing through the bore of member 52. A set may, for example, consist of four devices each with an abutment member 52 of different thickness. The practicioner can thus prepare several root canal insturments fitted with appropriate abutment devices, thereby avoiding having to turn around a device such as that of FIG. 7 during a treatment.

Figure 8:
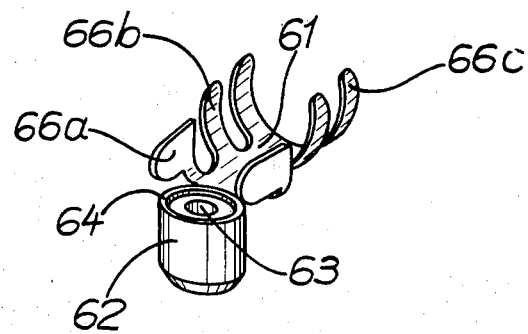
FIG. 8 is a perspective view of a sixth embodiment for attachment to a handpiece.

FIG. 8 shows a device for attachment to a handpiece. It comprises a fixed cylindrical abutment member 62 of given thickness, having a central bore 63 for passage of the instrument shank and a recessed upper face 64 for centring against the handpiece head. A thin stem 61 of arcuate section protruding transversely from the upper edge of member 62 has pairs of resilient lateral tabs 66a, 66b and 66c. Tabs 66a are forwardly directed to grip about flat side faces of the handpiece head, and tabs 66b, and 66c are curved to grip about the handpiece handle. A set of such devices each with a member 62 of given thickness will be selectively clipped to a handpiece to vary the penetration length of the root-canal instrument.

What is claimed is:

1. A penetration limiting device, for use with root canal instruments, comprising: an abutment consisting of a block defining an abutment having a bore extending therethrough and positioned to receive a shank portion of a root canal instrument extending through the bore when said device is clipped in use to the root canal instrument, said abutment means defining an abutment for limiting the penetration of the shank portion of the root canal instrument in use, and a resilient intermediate loop portion having two free ends relatively positionable by bending said loop portion, said abutment being mounted on one of said free end portions, the other of said free end portions together with said loop portion jointly comprising a clip for clipping the root canal instrument head between said free end portions, and said loop portion comprising a number of loops wherein the number of loops corresponds to the abutment bore length and to the depth at which said abutment limits penetration of the shank portion of the root canal instrument thereby to facilitate identification and selection of a device corresponding to a particular penetration depth.

2. A penetration limiting device according to claim 1, wherein said abutment comprises means defining an abutment of adjustable height in the direction of the bore extending therethrough for adjusting the penetration depth set by said abutment.

3. A penetration limiting device according to claim 2, wherein said abutment including an internally threaded bore extending therethrough, and an externally threaded screw for threading into said threaded bore, said screw having an axial bore extending therethrough for receiving the root canal instrument shank portion therethrough, said portion of said device including said threaded bore and said screw jointly comprising an abutment having a height determined by a distance said screw is threaded into said bore.

4. A penetration device according to claim 3, wherein said screw is between about four and six millimeters, and the depth of said threaded bore is sufficient to permit positioning of said screw at remote positions spaced about four millimeters.

5. A holder, for a dental root canal instrument, consisting of:
- a first block having first and second opposed major surfaces and having a bore extending through said block between said opposed major surfaces;
- a second block; and
- a resilient loop having a pair of free ends with said first and second blocks mounted on respective ones of the free ends.

6. A penetration limiting device for use with a dental root canal instrument, consisting of:
- a block having first and second opposed major surfaces and having a bore extending through said block between said opposed major surfaces;
- a rib extending from said block transversely to the bore extending through said block; and
- at least one pair of tabs extending from opposite sides of said rib for releasably engaging a body of a handpiece to releasably attach the penetration limiting device thereto.

* * * * *